US008518688B1

(12) United States Patent
Peterson et al.

(10) Patent No.: US 8,518,688 B1
(45) Date of Patent: *Aug. 27, 2013

(54) CULTURE MEDIUM FOR CULTIVATION OF MICROORGANISMS

(71) Applicant: Hardy Diagnostics, Santa Maria, CA (US)

(72) Inventors: Gary A. Peterson, Nipomo, CA (US); Andre Y. Hsiung, Santa Maria, CA (US)

(73) Assignee: Hardy Diagnostics, Santa Maria, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,534

(22) Filed: Oct. 17, 2012

Related U.S. Application Data

(60) Continuation of application No. 13/272,112, filed on Oct. 12, 2011, now Pat. No. 8,313,938, which is a division of application No. 10/832,496, filed on Apr. 26, 2004, now abandoned.

(51) Int. Cl.
*C12N 1/20* (2006.01)
*C12N 1/00* (2006.01)

(52) U.S. Cl.
USPC .................... 435/253.6; 435/253.4; 435/810; 435/885

(58) Field of Classification Search
None
See application file for complete search history.

(56) References Cited

U.S. PATENT DOCUMENTS

| | | | |
|---|---|---|---|
| 3,360,440 A * | 12/1967 | Haab et al. ....................... 435/34 |
| 3,616,251 A | 10/1971 | Linoli | |
| 3,699,003 A | 10/1972 | Kronish | |
| 4,288,543 A | 9/1981 | Sielaff | |
| 4,532,206 A | 7/1985 | Robinson | |
| 8,313,938 B1 | 11/2012 | Peterson | |

FOREIGN PATENT DOCUMENTS

| | | | |
|---|---|---|---|
| EP | 1098002 A1 | 5/2001 | |
| ES | 2048639 B1 | 3/1994 | |
| ES | 2088827 B1 | 9/1996 | |
| ES | 2153317 B1 | 2/2001 | |
| GB | 002 037 811 | * | 7/1980 |
| GB | 2037811 | | 7/1980 |
| WO | 0068417 A1 | 11/2000 | |

OTHER PUBLICATIONS

Difco Manual. 11th Edition, 1998, pp. 207-210, 232-234.*
Atlas R.M. In: Handbook of Microbiological Media. 1993. CRC Press. pp. 72, 112, 328, 380, 713, 848-850.
De La Rosa M, Perez M, Carazo C, Pareja L, Peis Ji, Hernandez F. New Granada Medium for detection and identification of group B streptococci. J Clin Microbiol. Apr. 1992;30(4):1019-21.
De La Rosa M, Villareal R, Vega D, Miranda C, Martinezbrocal A. Granada medium for detection and identification of group B streptococci. J Clin Microbiol. Oct. 1983;18(4):779-85.
Difco Manual. 11th Edition. 1998, pp. 207-210, 232-234.
Fallon RJ. The rapid recognition of Lancefield group B haemolytic streptococci. J Clin Pathol. Nov. 1974;27(11):902-5.
Gil EG, Rodriguez MC, Bartolomé R, Berjano B, Cabero L, Andreu A. Evaluation of the Granada agar plate for detection of vaginal and rectal group B streptococci in pregnant women. J Clin Microbiol. Aug. 1999;37(8):2648-51.
Higashide K, Keduka Y, Tanaka Y. Basic studies on group B streptococcal (GBS) culture medium. Rinsho Biseibutshu Jinsoku Shindan Kenkyukai Shi. Aug. 2000;11(1):39-45.
Holt J.G. In: Bergey's Manual of Systematic Bacteriology. vol. 2. 1986. Williams & Wilkins. p. 1051.
Hussain Z, Lannigan R, Stoakes L. A new approach for presumptive identification of clinically important streptococci. Zentralbl Bakteriol Mikrobiol Hyg A. Oct. 1984;258(1):74-9.
Islam AK. Rapid recognition of group-B Streptococci. Lancet. Jan. 29, 1977;1(8005):256-7.
Jewes LA, Jones D. Rapid method for the detection of group B streptococci from human sources. J Appl Bacteriol. Sep. 1986;61(3):219-23.
Lim DV, Morales WJ, Walsh AF. Lim group B Strep Broth and coagglutination for rapid identification of group B streptococci in preterm pregnant women. J Clin Microbiol. Feb. 1987;25(2):452-3.
Merritt K, Jacobs NJ. Characterization and incidence of pigment production by human clinical group B streptococci. J Clin Microbiol. Jul. 1978;8(1):105-7.
Merritt K, Jacobs NJ. Improved medium for detecting pigment production by group B streptococci. J Clin Microbiol. Oct. 1976;4(4):379-80.
Merritt K, Treadwell TL, Jacobs NJ. Rapid recognition of group B streptococci by pigment production and counterimmunoelectrophoresis. J Clin Microbiol. Mar. 1976;3(3):287-90.
Nguyen TM, Gauthier DW, Myles TD, Nuwayhid BS, Viana MA, Schreckenberger PC. Detection of group B streptococcus: comparison of an optical immunoassay with direct plating and broth-enhanced culture methods. J Matern Fetal Med. Jul.-Aug. 1998;7(4):172-6.
Noble MA, Bent JM, West AB. Detection and identification of group B streptococci by use of pigment production. J Clin Pathol. Mar. 1983;36(3):350-2.
Overman SB, Eley DD, Jacobs BE, Ribes JA. Evaluation of methods to increase the sensitivity and timeliness of detection of *Streptococcus agalactiae* in pregnant women. J Clin Microbiol. Nov. 2002;40(11):4329-31.

(Continued)

*Primary Examiner* — Vera Afremova

(57) ABSTRACT

The present invention discloses culture medium unit doses for cultivating microorganisms comprising at least two compositions, each composition packaged in a composition unit dose of a predetermined amount, said composition unit doses being used for combining one of each composition unit dose forming said culture medium unit dose. The composition unit doses being packaged separately and individually until a time said culture medium unit dose is to be prepared for use for cultivation of microorganisms, wherein said time one of each composition unit dose are combined thereby forming said culture medium unit dose. The invention also discloses a method of manufacturing the composition unit doses, and a kit for cultivating microorganisms, the kit comprising a combination of the composition unit doses.

17 Claims, No Drawings

(56) References Cited

OTHER PUBLICATIONS

Peterson G, Hsiung A, Blevins M, Mendes C et al. Evaluation of three methods (StrepB Carrot Broth™, LIM Broth, and Granada Agar) for recovery of group B streptococci. Poster Presentation at May 23-27 ASM 2004—New Orleans, Louisiana.

Reardon EP, Noble MA, Luther ER, Wort AJ, Bent J, Swift M. Evaluation of a rapid method for the detection of vaginal group B streptococci in women in labor. Am J Obstet Gynecol. Mar. 1, 1984;148(5):575-8.

Regan JA, Klebanoff MA, Nugent RP. The epidemiology of group B streptococcal colonization in pregnancy. Vaginal Infections and Prematurity Study Group. Obstet Gynecol. Apr. 1991;77(4):604-10.

Robinson-Dunn B, Bostic GD, Logue-O'Malley J. Evaluation of a modified granada medium for detection of *Streptococcus agalactiae* from vaginal-rectal specimens. Poster Presentation dated May 2003.

Rosa-Fraile M. Granada agar sensitivity and detection of group B streptococcus. J Clin Microbiol. Aug. 2003;41 (8):4007.

Rosa-Fraile M, Sampedro A, Rodriguez-Granger J, Garcia-Peña ML, Ruiz-Bravo A, Haïdour A. Pigment production by *Streptococcus agalactiae* in quasi-defined media. Appl Environ Microbiol. Jan. 2001;67(1):473-4.

Rosa-Fraile M, Rodriguez-Granger J, Cueto-Lopez M, Sampedro A, Gaye EB, Haro JM, Andreu A. Use of Granada medium to detect group B streptococcal colonization in pregnant women. J Clin Microbiol. Aug. 1999;37(8):2674-7.

Rosa-Fraile M, Sampedro A, Varela J, Garcia-Peña M, Gimenez-Gallego G. Identification of a peptide from mammal albumins responsible for enhanced pigment production by group B streptococci. Clin Diagn Lab Immunol. May 1999;6 (3):425-6.

Rosa-Fraile M, Sampedro A, Ruiz-Bravo A, Sanbonmatsu S, Gimenez-Gallego G. Identification of serum and urine proteins responsible for enhanced pigment production by group B streptococci as amylases. Clin Diagn Lab Immunol. Sep. 1996;3(5):594-6.

Schrag S, Gorwitz R, Fultz-Butts K, Schuchat A. Prevention of perinatal group B streptococcal disease. Revised guidelines from CDC. MMWR Recomm Rep. Aug. 16, 2002;51(Rr-11):1-22.

Schrag SJ, Zell ER, Lynfield R, Roome A, Arnold KE, Craig AS Harrison LH, Reingold A, Stefonek K, Smith G, Gamble M, Schuchat A; Active Bacterial Core Surveillance Team. A population-based comparison of strategies to prevent early-onset group B streptococcal disease in neonates. N Engl J Med. Jul. 25, 2002;347(4):233-9.

Schuchat A. Group B streptococcal disease: from trials and tribulations to triumph and trepidation. Clin Infect Dis. Sep. 15, 2001;33(6):751-6. Epub Aug. 10, 2001.

Spellerberg B, Pohl B, Haase G, Martin S, Weber-Heynemann J, Lütticken R. Identification of genetic determinants for the hemolytic activity of *Streptococcus agalactiae* by ISS1 transposition. J Bacteriol. May 1999;181(10):3212-9.

Uh Y, Jang IH, Hwang GY, Yoon KJ. Serotypes and biochemical reaction patterns of group B streptococci. Korean J Clin Pathol. Sep. 18, 1998;3(3):386-390.

Waitkins SA. Evaluation of rapid methods of identifying group B streptococci. J Clin Pathol. Mar. 1980;33(3):302-5.

Wilkinson HW. CAMP-disk test for presumptive identification of group B streptococci. J Clin Microbiol. Jul. 1977;6(1):42-5.

\* cited by examiner

CULTURE MEDIUM FOR CULTIVATION OF MICROORGANISMS

CROSS-REFERENCE TO RELATED APPLICATIONS

This application is a continuation of U.S. application Ser. No. 13/272,112, filed Oct. 12, 2011, which is incorporated herein by reference, which is a divisional of U.S. application Ser. No. 10/832,496, filed Apr. 26, 2004, which is incorporated herein by reference.

TECHNICAL FIELD

The present invention relates to culture medium unit doses for cultivation of microorganisms. More specifically, the present invention relates to unit doses of compositions of culture medium and methods of manufacture and use of composition unit doses to form culture medium unit doses. Even more specifically, the present invention relates to culture medium unit doses and methods of manufacture and use of culture medium unit doses useful for extending the shelf life of culture medium.

BACKGROUND OF THE ART

Cultivation of microorganisms in culture medium, also known as growth medium, has been and continues to remain a fundamental cornerstone of the practice of microbiology, and extends back to the origins of the science. Cultivation of microorganisms is growth of microorganisms for the purposes of propagation, isolation, purification, differentiation, selection, identification, and determination of antibiotic susceptibility. It has long been recognized that microorganisms require sources of nutrients for growth. Such nutrients are provided in sterile preparations formulated to provide a nutrient environment advantageous to cultivating a microorganism of interest. Often nutrients are provided in either liquid form, commonly known as broth, or in solid form, which is usually a broth with a gelling agent such as agar, gelatin, or pectin included as an ingredient, often referred to simply as agar.

Many culture medium compositions have been developed for specific purposes and to meet specific nutritional requirements of various microorganisms, many of which exhibit specific nutritional requirements in addition to nutrients found in traditional culture media. Successful cultivation of specific microorganisms often requires supplements including blood, blood products, vitamins, and amino acids to be included in the growth medium. Cultivation processes may also require inclusion of inhibitors such as antibiotics for suppression of growth of microorganisms not of interest while permitting growth of microorganisms of interest.

Culture medium compositions have also been developed to selectively cultivate a microorganism of interest from a mixed population of microorganisms. Selective cultivation of microorganisms from a mixed population of microorganisms is most commonly accomplished by including in the culture medium one or more compounds which are inhibitory to those microorganisms in a mixture which are not of interest, yet is not inhibitory to the microorganism of interest. Antibiotics are often used as selective inhibitory compounds included in selective culture medium.

Other culture medium compositions have also been developed which differentiate a microorganism of interest from those not of interest. Differential culture medium often contains components to which various microorganisms respond differently, most often producing a visual means for distinguishing between microorganisms. For example, chromogenic substrates have been used to distinguish between microorganisms producing a specific enzyme and other which do not produce the specific enzyme, thus differentiating one from the other.

Culture medium may include a wide variety of components, for example, nutrients, essential nutrients, essential elements, growth promoters, selective inhibitors, environmental conditioners, environmental controllers, indicators of biochemical reactions, end product detectors, biochemical reaction substrates, and enzyme substrates. Culture medium recipes may be developed to improve cultivation of specific microorganisms by including components advantageous to cultivation of the specific organism of interest. Some culture medium components, while required for a specific function are prone to degradation under various environmental conditions related to preparation, transportation, or storage of a culture medium. Such environmental conditions may include, but are not limited to, temperature extremes, light exposure, atmosphere condition, pH, oxidation-reduction state, ionic state, mineral salt concentration, humidity, or moisture. Components may be particularly unstable while in a liquid environment which is commonly the physical state of culture medium.

A common problem encountered in clinical microbiology laboratories is cultivation, isolation, and identification of many pathogenic microorganisms, requires specialized culture media, which often contains components that are not stable under common storage conditions. Microorganisms causing human and animal disease, may occur infrequently and may also require specialized culture medium for propagation, selection, differentiation, identification and susceptibility testing, yet a clinical microbiology laboratory must maintain the capacity to cultivate these microorganisms on short notice. Consequently, many laboratories are faced with the inefficiency of maintaining specialized culture medium which may have a short shelf life, and which becomes degraded before it is used.

Many culture medium components are degraded or destroyed by commonly employed methods of culture medium production, which may require preparing a solution of components in a liquid diluent, most often water, sterilizing the mixture by autoclaving, steam pressurized to 15 psi, 121° C., for at least 15 minutes, followed by cooling. To avoid such component degradation, a mixture of heat labile components may be prepared and sterilized by non destructive means, for example, by filtration through a membrane filter, and the filter sterilized heat labile mixture may be added to the cooled autoclaved mixture. Some components may require no sterilization process, for example, blood, blood cells, serum, or plasma, but, nonetheless may be labile. Such components may be added directly to the autoclaved medium.

A number of commercial culture medium manufacturers provide supplement preparations for addition to culture medium in quantities sufficient to manufacture large batches of culture medium. Culture medium is routinely manufactured by preparing the culture medium in a large batch, and after cooling the culture medium, any labile supplements are added. Only after the culture medium is completed in batch, is the culture medium dispensed into individual containers such as tubes, bottles, or Petri plates used for distribution to users. These containers of culture medium are routinely used for cultivation of a single sample, specimen or microorganism and constitute a culture medium unit dose.

The process has several disadvantages. First, the manufacturing process is complex requiring careful handling, transferring, mixing and dispensing sterile products while avoiding contamination resulting in expensive, inefficient manufacturing, high potential for contamination, and difficulty in quality control. Second, this process does not allow a culture medium unit dose to be dispensed until after all components have been added to the mixture, the mixture then cannot readily or economically be resterilized. This requires the mixture be dispensed into culture medium unit doses under aseptic conditions, resulting in a high risk of contamination. Third, once a labile component has been added to the mixture, the culture medium stability or shelf life is substantially reduced. Fourth, due to a short shelf life, the end user laboratory is subject to loss of the culture medium due to degradation of the culture medium before it can be used.

Yet another manufacturing process has been to prepare culture medium as described, and then after dispensing culture medium unit doses, to dry the culture medium, requiring rehydration prior to the time of use. Culture media are dried by one of several alternative processes including forced air, vacuum, freeze drying, heat, or combinations of these processes. Drying has several disadvantages. First, it is an expensive and time consuming manufacturing process requiring extensive handling of the medium. The drying process does not lend itself to continuous processing, but requires batch processing. Additional handling steps increases the risk of contamination. Second, many culture medium components do not readily dry completely. They form a viscous liquid containing tightly bound water resulting in poor stability and difficulty in rehydrating the culture medium. Even when completely dried the components are extremely hygroscopic and easily become moist, losing stability. Third, once dried, the components may individually or collectively be resistant to dissolution in a diluent. Such components may require special procedures to dissolve in diluent, for example first dissolving in acid or an organic solvent prior to diluting with diluent. Fourth, a separate sterile diluent must be prepared and used, thereby increasing cost, complexity of use, and increased risk of contamination.

What is needed is a culture medium unit dose which offsets the problems discussed. A culture medium unit dose having its components packaged and maintained in separate component unit doses would provide the means to manufacture, package, ship, and store each composition unit dose under conditions best suited for the specific composition unit dose, for example one composition unit dose may be most stable when in a dry state, another may be most stable at freezing temperature, yet another may be most stable when protected from light, and yet another may be sufficiently stable to tolerate storage at room temperature. Further, what is also needed is a means to provide culture medium unit dose which can be maintained for long periods of time in expectation of infrequent need to use the culture medium unit dose. What is needed is a culture medium unit dose which is not constructed until the time the culture medium is needed for use. Having the culture medium unit dose packaged as individual composition unit doses, each stored for optimum stability, to be combined forming the culture medium dose at or near the time of intended use is needed. The present invention addresses these needs.

SUMMARY

The foregoing need for long shelf life culture medium unit doses is met by the present invention which provides culture medium unit dose for cultivating microorganisms comprising at least two compositions, each composition packaged in a composition unit dose of a predetermined amount, said composition unit doses being used for combining one of each composition unit dose forming said culture medium unit dose. The composition unit doses being packaged separately and individually until a time said culture medium unit dose is to be prepared for use for cultivation of microorganisms, wherein said time one of each composition unit dose are combined thereby forming said culture medium unit dose.

The foregoing need for long shelf life culture medium unit doses is met by the present invention which provides a method of manufacture of culture medium unit dose for cultivation of microorganisms, comprising, providing at least two compositions, dispensing and packaging each composition in a composition unit dose of a predetermined amount. The method further comprises maintaining said composition unit doses separately and individually until a time said culture medium unit dose is to be prepared for use for cultivation of microorganisms, and preparing said culture medium unit dose by combining one of each composition unit dose at said time, thereby forming said culture medium unit dose.

The foregoing need for long shelf life culture medium unit doses is met by the present invention which provides a kit for cultivation of microorganisms, the kit comprising, a culture medium unit dose, said culture medium unit dose comprising at least two compositions, each composition packaged in an individual unit dose of a predetermined amount, wherein one unit dose of each composition is combined thereby forming a single use unit dose of a culture medium for use for cultivation of microorganisms. The kit maintains the composition unit doses separately and individually until a time said culture medium unit dose is to be prepared for use for cultivation of microorganisms, wherein at said time one of each composition unit dose are combined thereby forming said culture medium unit dose.

The present invention may be applied, for example, to any number of preselected culture media, recipes for which are given in various publications, by application of the invention to a preselected recipe.

DETAILED DESCRIPTION OF THE INVENTION

The present invention provides a solution to the problem of short shelf life of batch prepared culture medium containing labile components, by providing a plurality of composition unit doses, each composition being derived from a culture medium recipe to contain compatible ingredients, for example a first composition may contain only steam sterilized ingredients, a second composition may contain only filter sterilized ingredients, and a third composition may contain only a normally sterile component such as serum. Each composition may be dispensed into composition unit doses, each measured to fulfill the requirement of a culture medium when combined with other composition unit doses. The component unit doses may be prepared and packaged to be efficiently stored to preserve the integrity of the composition, the storage conditions being independent of the storage conditions of the other composition unit doses of culture medium. Depending on the characteristics of each composition, it may be dried, concentrated, dispensed without change into a composition unit dose container such as an inert carrier, sealed pouch, tube, bottle, ampoule, vial, or the like. Examples include light shielded containers, i.e. foil, brown, opaque, vacuum stored, stored under specific gas, or in sealed glass containers.

The composition unit doses may be stored separately and independently at respective optimum storage conditions until culture medium unit dose is to be used. At that time one of each composition unit dose is mixed together to form a culture medium unit dose.

The present invention provides a number of advantages.

First, flexibility; the individual composition unit doses are made by the most cost efficient means, determined by the specific characteristics of the components comprising the composition. Typically a heat stable composition may be prepared in batch form, dispensed into composition unit doses, and the composition unit doses steam sterilized. Other composition unit doses may be most advantageously prepared in the most cost efficient mean independent of other compositions. For example a composition may be prepared in batch form, filter sterilized, dispensed into composition unit doses, and the composition unit doses stored under conditions appropriate to the particular composition.

Second, preparation of individual composition unit doses may be stored independently of other composition unit doses under storage conditions advantageous for each composition resulting in a shelf life longer than that of the complete culture medium. The culture medium unit dose may be prepared at the time of intended use by preparing a mixture comprising one of each composition unit dose required for the culture medium.

Third, laboratories may maintain stocks of component unit doses for infrequently used but essential culture medium for long periods. A culture medium unit dose may be prepared at the time of intended use. As many culture medium unit doses as may be required may be prepared at the time of intended use.

There is no indication of the present use, namely, making, providing, and using component unit doses, to prepare and use culture medium unit doses for cultivation of microorganisms.

The present invention provides a culture medium unit dose, a method of making a culture medium unit dose using composition unit doses, and a kit comprising composition unit doses. The invention is useful for use with many culture medium formulations for cultivation, propagation, selection, differentiation, identification and susceptibility testing of microorganisms.

It is understood that the culture medium may be derived from a preselected culture medium recipe; that the individual compositions may be prepared in amounts and concentrations to be specific to the recipe, be complementary to one another, and to meet the requirements of the recipe, on combining a unit dose of each composition. The culture medium unit dose is formed according to a preselected recipe. The culture medium unit dose is formed only at the time of mixing together composition unit doses specific to a preselected recipe.

It is further understood that composition unit doses are formulated such that a culture medium unit dose is formed by combination of one of each composition unit dose defining the culture medium. A culture medium unit dose is typically from about 1 ml to about 10 ml, but may be as little as about 0.1 ml or as much as about 25 ml. A culture medium unit dose is typically contained within a vessel such as a petri dish, tube, bottle, ampoule, or the like.

The composition unit dose packaging compositions may vary widely. A composition unit dose may be provided in a variety of containers including tubes, bottles, and ampoules. A composition unit dose container may be used as a final receptacle for a culture medium unit dose, or it may be used as an intermediate mixing container in which composition unit doses may be mixed forming a culture medium unit dose and subsequently transferring the culture medium unit dose to a more appropriate container, for example, a petri dish. Composition unit doses may also be supplied in a variety of formats including being dried in an carrier matrix, such as paper, glass wool, glass beads, plastic beads, gelatin, agar, starch, protein, contained in sealed pouches, contained in dissolvable capsules, contained in non dissolvable capsules to be crushed to release the composition unit dose, formed into dissolvable tablets, contained in a sealed container such as a pouch, envelope, bottle, vial, or tube or being liquid in sealed ampoules, vials, or tubes. In the case of dried composition unit doses it is further understood that the composition unit dose may be packaged individually in a sealed container or may be packaged in multiples in a single container from which individual composition unit doses may be removed as needed.

A first embodiment is a liquid culture medium unit dose in which a first composition unit dose is an amount of about 10 ml contained in a screw capped test tube, the first composition unit dose having been prepared according to a preselected recipe in which the first composition components are dissolved in diluent and dispensed into the unit dose before being sterilized. The first embodiment further comprises a second composition unit dose prepared by dispensing a preselected quantity of sterile liquid second composition into a plurality of paper disks, drying the impregnated paper disks and storing the dried impregnated paper disks in a resealable screw capped vial also containing a desiccant pouch. The culture medium unit dose is made by transferring one dried impregnated paper disk from the vial to the tube containing the first composition unit dose and shaking the tube to elute the second composition unit dose from the disk thereby forming a culture medium unit dose.

A second embodiment is an agar containing culture medium unit dose for preparing a solid culture medium, in which the first composition unit dose is an amount of about 10 ml contained in a screw capped test tube, having been prepared according to a preselected recipe in which the first composition components are dissolved in diluent and dispensed into the unit dose before being sterilized. The first composition contains an amount of gelling agent, typically, for example, agar, to effectively solidify the culture medium. It is understood that upon cooling, the first composition unit dose will solidify into a gel. The second embodiment further comprises a second composition unit dose prepared by dispensing a preselected quantity of sterile liquid second composition solution into a plurality of screw capped vials and storing the filled vials frozen. The second composition unit dose may be about 1 ml volume. The culture medium unit dose is made by melting a first composition unit dose, holding it at a temperature compatible with maintaining the first composition unit dose in a melted liquid state and compatible with maintaining stability of the second composition unit dose for a short period of time, thawing a second composition unit dose, transferring the second composition unit dose from the vial to the tube containing the melted liquid first composition unit dose, mixing the tube contents, forming a culture medium unit dose, and transferring the culture medium unit dose to an appropriate final container such as a petri dish in which the culture medium unit dose is allowed to cool and solidify.

A third embodiment is a liquid culture medium unit dose in which a first composition unit dose is an amount of about 10 ml contained in a screw capped test tube, the first composition unit dose having been prepared according to a preselected recipe in which a first selected group of components may be dissolved in a diluent, steam sterilized, and then cooled. A second selected group of components may be dissolved in a diluent, filter sterilized, and mixed with the solution of the first selected group of components, and the mixture dispensed into sterile containers. A second composition unit dose may prepared by dispensing a preselected quantity of sterile liquid second composition into a plurality of paper disks, drying the impregnated paper disks and storing the dried impregnated paper disks in a resealable screw capped vial also containing a desiccant pouch. The culture medium unit dose is made by transferring one dried impregnated paper disk from the vial to the tube containing the first composition unit dose and shaking the tube to elute the second composition unit dose from the disk thereby forming a culture medium unit dose.

The descriptions discussed herein in relation to the present invention represent preferred embodiments of the present invention. It is understood that these embodiments are not contemplated to be the only possible embodiments.

EXAMPLES

The following examples are intended to illustrate, but not limit, the present invention. Accordingly, variations and equivalents, now known or later developed, that would be within the purview of one skilled in this art are to be considered to fall within the scope of this invention, which is limited only as set forth by the appended claims.

Preparation of culture medium unit dose for cultivation, selection, differentiation, and identification of *Streptococcus agalactiae*, Lancefield group B streptococcus (GBS).

GBS is a bacterium often found in the human genitourinary tract and is an important etiologic agent of neonatal sepsis and meningitis. Detection of GBS requires sampling the vaginal and rectal areas of pregnant women and isolating and identifying GBS from specimens contaminated with other microorganisms. A culture medium for selective enrichment of GBS, differentiation of GBS from other microorganisms, and identification of GBS is made according to the following recipe:

First Composition Unit Dose
Component Group 1, formula per liter of medium:

| | |
|---|---|
| Proteose peptone #3 | 25.0 g |
| Starch, soluble | 10.0 g |
| (3-N-morpholino) propanesulfonic acid (MOPS) | 11.0 g |
| Sodium phosphate, dibasic | 8.5 g |
| L-cysteine | 0.5 g |
| Deionized water | 990 ml |

Mix all of the ingredients of Component Group 1 and the deionized water; heat with stirring to boiling; boil 1 minute; autoclave 121° C., 15 minutes; cool to room temperature; adjust pH to 7.4.

Component Group 2, formula per liter of medium:

| | |
|---|---|
| d-glucose | 250 G |
| Pyruvic acid, sodium salt | 100 g |
| Magnesium sulfate, anhydrous | 20 g |
| Methotrexate, sodium salt | 0.6 g |
| Crystal violet | 0.02 g |
| Colistin sulfate | 0.5 g |
| Metronidazole | 1 g |
| Deionized water | 250 ml |

Mix all of the ingredients of Component Group 2 and the deionized water; dissolve the ingredients with stirring, but no heat, sterilize the solution by filtering through a 0.2µ membrane filter.

First composition unit dose is made by aseptically adding 10 ml of Component Group 2 to 990 ml of Component Group 1; mixing well; aseptically dispensing 4 ml of mixture into sterile 13×100 mm screw capped tubes; cap the tubes and store at 2-8° C. The first composition unit dose is stable for at least 4 months.

Second Composition Unit Dose
Component Group 2, formula per liter of medium:

| | |
|---|---|
| Sterile horse serum | 500 ml |
| Schleicher & Schuell ® #900 paper disks, ¼" diameter (or equivalent), sterile | 1000 |

Place disks in a single layer on a screen. Place a second screen on top of the disks and secure the two screens together so the disks are held between the screens. Place the disk screen assembly into fresh sterile horse serum, and allow the disks to saturate with sterile horse serum. Remove the disk screen assembly from the horse serum; place the disk screen assembly into a forced air desiccator with air movement, but no heat for 24 hours. After drying, remove the disks and dispense 20 disks each into amber screw cap jars. Include a 0.5 gm desiccant packet in each jar. Each dry impregnated disk represents one second composition unit dose. Store the bottle at 2-8° C. The Second composition unit dose is stable for at least 3 months.

Culture Medium Unit Dose

At the time of use, allow a first composition unit dose tube to come to room temperature. Allow the closed bottle containing second composition unit dose disks to come to room temperature without opening the bottle. Transfer one second composition unit dose disk from the bottle to the first composition unit dose tube; close the tube, and invert the tube to elute the horse serum from the second composition unit dose disk and to mix any precipitate, forming the culture medium unit dose.

Use of the Culture Medium Unit Dose

Inoculate the culture medium unit dose by inserting a swab containing a vaginal or rectal sample into the tube. Break the swab, leaving the sample end in the tube. Incubate the inoculated tube at 35° C. for 24 hours.

The tube is observed after 6 hours and again after 24 hours incubation for evidence of color development. Any degree of orange to red color development within the broth and/or paper disk is considered as a positive reaction and evidence of presence of GBS in the specimen.

Example 2

Preparation of Culture Medium for Cultivation, Isolation, and Susceptibility Testing of Mycobacteria Including *Mycobacterium tuberculosis*. (Middlebrook 7H10 agar with Oleic acid Albumin Dextrose Catalase (OADC) Supplement)

Mycobacteria and especially *Mycobacterium tuberculosis* are bacteria which cause serious human and animal infection. Detection of mycobacteria requires isolating and identifying mycobacteria from specimens such as sputum and urine which may be contaminated with other microorganisms. Mycobacteria often grow more slowly that other contaminating bacteria, and consequently require supplementation for improved isolation and growth. The medium is supplemented with a composition, AODC, which is unstable in the presence of light, consequently reducing the effective shelf life of the medium. A supplemented culture medium for cultivation, isolation, and susceptibility testing of mycobacteria is made according to the following recipe:

First Composition Unit Dose

First Composition, formula per liter of medium:

| | | |
|---|---|---|
| Disodium phosphate | 1.5 | g |
| Monopotassium phosphate | 1.5 | g |
| L-glutamic acid | 0.5 | g |
| Ammonium sulfate | 0.5 | g |
| Sodium citrate | 0.4 | g |
| Ferric ammonium citrate | 40 | mg |
| Magnesium sulfate | 25 | mg |
| Zinc sulfate | 1 | mg |
| Copper sulfate | 1 | mg |
| Pyridoxine | 1 | mg |
| Calcium Chloride | 0.5 | mg |
| Biotin | 0.5 | mg |
| Malachite green | 0.25 | mg |
| Glycerol | 5 | ml |
| Agar | 15 | g |
| Deionized water | 995 | ml |

Combine all first composition components including deionized water, except glycerol. Heat with stirring until the mixture boils. Boil for 1 min. Add glycerol and continue mixing. Prepare first composition unit dose by dispensing 10 ml into 13×100 mm screw capped tubes; autoclave 121° C., 10 minutes; cool to room temperature; final pH 6.8.

Second Composition Unit Dose

Second Composition, formula per 100 ml of medium:

| | | |
|---|---|---|
| Bovine albumin | 50 | g |
| Dextrose | 20 | g |
| Sodium chloride | 8.5 | g |
| Catalase, beef | 40 | mg |
| Oleic acid | 0.5 | g |
| Deionized water | 100 | ml |

Mix all of the ingredients of second composition and the deionized water; dissolve the ingredients with stirring, but no heat; sterilize the solution by filtering through a 0.2µ membrane filter. To make the second composition unit dose, dispense 1 ml into sterile screw capped vials, store vials at 2-8° C., in the dark.

Culture Medium Unit Dose

At the time of use, heat a first composition unit dose tube in an autoclave or a heated water bath until the media melts, about 60° C. Maintain the first composition unit dose melted, about 45° C. in a heated water bath. Allow a second composition unit dose vial to come to room temperature without opening the vial. Transfer the entire volume of the second composition unit dose vial from the vial to the first composition unit dose tube, close the tube and gently mix the tube, forming the culture medium unit dose. Pour the culture medium unit dose into a petri plate and allow the petri plate to sit undisturbed until the medium solidifies. Alternatively, the tube of culture medium unit dose may be tilted and allowed to solidify, resulting in a tube slant of culture medium unit dose.

Inoculate the culture medium unit dose petri plate or tube slant by placing a portion of a specimen on the surface of the culture medium and spreading the specimen over the surface with a sterile inoculating device. Incubate the inoculated petri plate or tube at 35° C. for up to 6 weeks.

The petri plate or tube is observed daily for several days and weekly thereafter for evidence of growth. Any observed bacteria colonies are investigated as potential colonies of mycobacteria by conventional microbiological methods.

Example 3

Preparation of Culture Medium Unit Dose for Cultivation, and Susceptibility Testing of *Haemophilus Influenzae* (Haemophilus Test Medium (HTM))

Increasing incidence of antibiotic resistant strains of *Haemophilus influenzae* has underscored the need for a reliable susceptibility test method for this organism. Modifications of standard procedures have become necessary because of the fastidious nature of *H. influenzae*. Complex growth additives may cause antagonism of certain antibiotics and have shown poor reproducibility. HTM is an improved culture medium for *H. influenzae*.

First Composition Unit Dose

First Composition, formula per liter of medium:

| | | |
|---|---|---|
| Acid hydrolysis of casein | 17.5 | g |
| Yeast extract | 5 | g |
| Beef extract | 2 | g |
| Starch | 1.5 | g |
| Agar | 17 | g |
| Deionized water | 1000 | ml |

Combine all first composition components including deionized water. Heat with stirring until the mixture boils. Boil for 1 min. Prepare first composition unit dose by dispensing 10 ml into 13×100 mm screw capped tubes; autoclave 121° C., 10 minutes; cool to room temperature; final pH 7.3.

Second Composition Unit Dose

Second Composition, formula per 100 ml of medium:

| | | |
|---|---|---|
| Hematin | 49.5 | g |
| Nicotinamide adenosine dinucleotide (NAD) | 49.5 | mg |
| Deionized water | 100 | ml |

Mix all of the ingredients of second composition and the deionized water; dissolve the ingredients with stirring, add 1 N sodium hydroxide as needed to dissolve the hematin. Heat to boiling. Boil 1 min. Adjust the pH to 7.3. Sterilize the solution by filtering through a 0.2µ membrane filter. To make the second composition unit dose, dispense 3 ml into sterile screw capped vials, store vials at 2-8° C., in the dark.

Culture Medium Unit Dose

At the time of use, heat a first composition unit dose tube in an autoclave or a heated water bath until the media melts, about 60° C. Maintain the first composition unit dose melted, about 45° C. in a heated water bath. Allow a second composition unit dose vial to come to room temperature without opening the vial. Transfer the entire volume of the second composition unit dose vial from the vial to the first composition unit dose tube, close the tube and gently mix the tube, forming the culture medium unit dose. Pour the culture medium unit dose into a petri plate and allow the petri plate to sit undisturbed until the medium solidifies.

Inoculate the culture medium unit dose petri plate by placing a portion of a specimen on the surface of the culture medium and spreading the specimen over the surface with a sterile inoculating device. Drop an antibiotic containing disk onto the agar surface. Incubate the inoculated petri plate or tube at 35° C. for 24 hours.

The petri plate is observed after 24 hours incubation for evidence of growth inhibition around the antibiotic containing disk.

It is understood that the foregoing examples are considered illustrative only of the principles of the invention. Further, since numerous modifications and changes will readily occur to those skilled in the art, it is not desired to limit the invention to the exact construction and operation shown and, accordingly, all suitable modifications and equivalents may be resorted to, falling within the scope of the invention.

What is claimed is:

1. A kit for forming a single unit dose of a liquid culture medium for detection of Group B Streptococcus (GBS) by orange to red color development, said kit comprising:
   a. A liquid culture medium unit dose comprising starch; and
   b. Separately, a serum unit dose dried in a carrier;
   Wherein one unit dose of each of (a) and (b) when combined forms said single unit dose of a culture medium for detection of GBS by orange to red color development.

2. The kit of claim 1, wherein said unit dose of (a) further comprises peptone.

3. The kit of claim 1, wherein said unit dose of (a) further comprises methotrexate.

4. The kit of claim 1, wherein said unit dose of (a) further comprises magnesium sulfate.

5. The kit of claim 1, wherein said unit dose of (a) further comprises glucose.

6. The kit of claim 1, wherein said unit dose of (a) further comprises pyruvate.

7. The kit of claim 1, wherein said unit dose of (a) further comprises phosphate and MOPS buffer, with said unit dose of (a) at pH 7.4.

8. The kit of claim 1, wherein said unit dose of (a) further comprises crystal violet.

9. The kit of claim 1, wherein said unit dose of (a) further comprises colistine sulfate.

10. The kit of claim 1, wherein said unit dose of (a) further comprises metronidazole.

11. The kit of claim 1, wherein said unit dose of (a) is contained in a tube.

12. The kit of claim 1, wherein said unit dose of (a) is made by autoclaving a composition comprising starch, peptone and phosphate and MOPS buffer.

13. The kit of claim 1, wherein said unit dose of (a) is made by adding a second composition comprising glucose and pyruvate to a first composition comprising starch, peptone and phosphate and MOPS buffer, after autoclaving said first composition.

14. The kit of claim 1, wherein, at the time of GBS inoculation, said unit dose of (b) is added to said unit dose of (a).

15. The kit of claim 1, wherein a plurality of said unit dose of (b) is packaged in a single container.

16. The kit of claim 1, wherein the formula for said unit dose of (a) is 10 g of starch per liter of medium.

17. The kit of claim 1, wherein the formula for said unit dose of (a) is 0.6 g of methotrexate sodium salt per liter of medium.

* * * * *